United States Patent
Wiltshire

(10) Patent No.: US 6,171,288 B1
(45) Date of Patent: Jan. 9, 2001

(54) OSTOMY BAG

(75) Inventor: Neil Philip Wiltshire, East Sussex (GB)

(73) Assignee: Salt & Son Limited, Birmingham (GB)

( * ) Notice: Under 35 U.S.C. 154(b), the term of this patent shall be extended for 0 days.

(21) Appl. No.: 09/484,737

(22) Filed: Jan. 18, 2000

(30) Foreign Application Priority Data

Jan. 19, 1999 (GB) .................................................. 9900992

(51) Int. Cl.$^7$ ..................................................... A61F 5/44
(52) U.S. Cl. ............................................................. 604/333
(58) Field of Search ..................................... 604/327, 328, 604/331, 332, 334, 335, 337, 338, 339, 340, 341, 342, 333

(56) References Cited

U.S. PATENT DOCUMENTS

| 4,411,659 | 10/1983 | Jensen et al. . |
| 5,672,163 | 9/1997 | Ferreira et al. ....................... 604/333 |
| 5,690,623 | 11/1997 | Lenz et al. . |
| 5,865,819 | * 2/1999 | Cisko, Jr. et al. ................... 604/339 |

FOREIGN PATENT DOCUMENTS

| 0 852 936 | 7/1998 | (EP) . |
| 2 116 433 | 9/1983 | (GB) . |
| 2139501 | 11/1984 | (GB) . |
| 2149306 | 6/1985 | (GB) . |
| 2 265 832 | 10/1993 | (GB) . |
| 2 290 712 | 1/1996 | (GB) . |
| 2311014 | 9/1997 | (GB) . |

* cited by examiner

Primary Examiner—John G. Weiss
Assistant Examiner—Ann Y. Lam
(74) Attorney, Agent, or Firm—Marshall, O'Toole, Gerstein, Murray & Borun

(57) ABSTRACT

A vented ostomy bag with a gas filter is described, the bag having a top and a bottom and comprising first and second outer walls sealed around their edges, the first outer wall incorporating a stoma-receiving opening. The bag further comprises first and second intermediate walls also sealed with the first and second outer walls around their edges to provide between the first outer and first intermediate walls a first chamber, between the first and second intermediate walls a second chamber and between the second intermediate and second outer walls a third chamber. A first gas vent is provided in the first intermediate wall between the first and second chambers for the passage of gas there between, and a second gas vent is provided in the second intermediate wall between the second and third chambers for the passage of gas there between. A gas passage is provided from the third chamber out of the bag which passes through the gas filter.

11 Claims, 2 Drawing Sheets

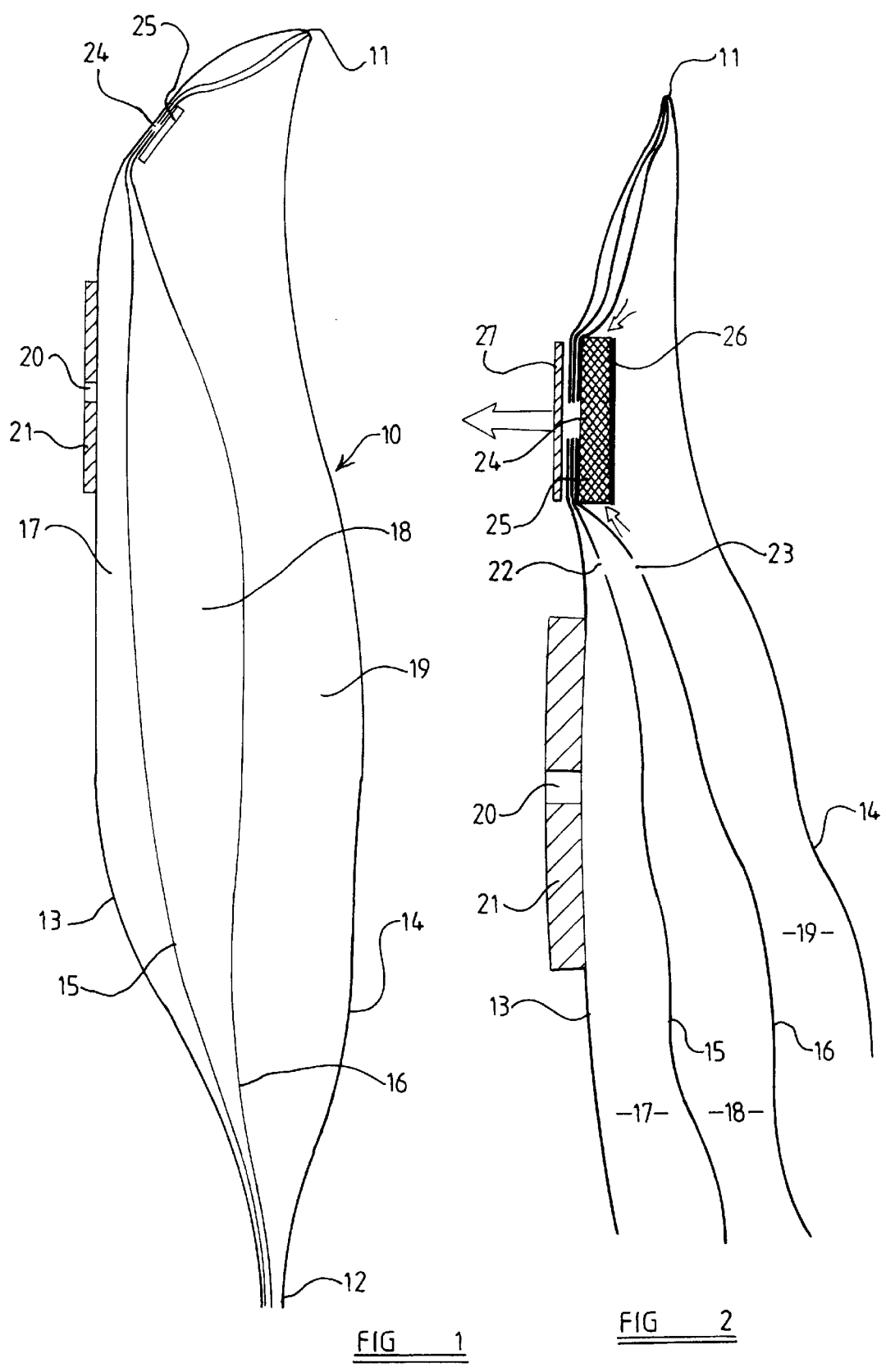

OSTOMY BAG

BACKGROUND TO THE INVENTION

The invention relates to an ostomy bag, and in particular to a vented bag with a gas filter.

Ostomy bags incorporating gas filters are known and examples are described in GB 2 116 433 and EP 0 852 936.

The first of these earlier patent documents, GB 2 116 433, describes an ostomy bag having two outer walls, one intermediate wall and two chambers. The ostomy-receiving opening is provided in one outer wall, a gas vent is provided in the intermediate wall and a gas passage is provided in the second outer wall which is also fitted with a gas filter. The upper portion of the intermediate wall is embossed to help prevent the various walls sticking together and inhibiting gas flow.

The second of these earlier patent documents, EP 0 852 936, describes an ostomy bag having two outer walls, one full and one partial intermediate wall, and two chambers. The partial intermediate wall is located in the upper portion of the second chamber. The ostomy-receiving opening is provided in the first outer wall, gas vent is provided in the full intermediate wall and a gas passage is provided in the other outer wall which is also provided with a gas filter.

One of the problems experienced by users of vented ostomy bags with gas filters is the blocking of the gas filter by solids or liquids. The division of the ostomy bags into two chambers and the provision of complex gas paths through the bags to the filter are attempts to reduce the occurrence of this problem. However, the known products are not completely successful at overcoming the problems described.

SUMMARY OF THE INVENTION

It is an object of the present invention to provide an alternative form of ostomy bag with a gas filter which mitigates the above described problems.

According to the present invention there is provided a vented ostomy bag with a gas filter, the bag having a top and a bottom and comprising first and second outer walls sealed around their edges, the first outer wall incorporating a stoma-receiving opening; wherein the bag further comprises first and second intermediate walls also sealed with the first and second outer walls around their edges to provide between the first outer and first intermediate walls a first chamber, between the first and second intermediate walls a second chamber and between the second intermediate and second outer walls a third chamber; a first gas vent being provided in the first intermediate wall between the first and second chambers for the passage of gas there between, a second gas vent being provided in the second intermediate wall between the second and third chambers for the passage of gas there between, and a gas passage being provided from the third chamber out of the bag which passes through the gas filter.

The walls are conveniently formed of thermoplastics material and are sealed at their edges by welding.

Preferably the gas passage is provided through the second intermediate wall, the first intermediate wall and the first outer wall.

The gas filter, the second intermediate wall, the first intermediate wall and first outer wall are conveniently all welded together to provide the gas passage from the third chamber out of the bag.

The gas filter may be provided within the third chamber on the second intermediate wall.

Preferably the gas filter, first gas vent and second gas vent are all provided between the stoma-receiving opening and the top of the bag.

In addition the gas filter, first gas vent and second gas vent are preferably laterally disposed with respect to each other.

Conveniently the gas filter is located substantially centrally of the width of the bag, the first gas vent is laterally disposed to one side of the gas filter and the second gas vent is laterally disposed to the other side of the gas filter.

The first and second gas vents may comprise "S" shaped cuts in the respective intermediate walls.

The portions of one or both of the intermediate walls between the ostomy-receiving opening and the top of the bag may have surfaces which are non-smooth. The non-smooth surface(s) may be formed by embossing of the intermediate wall(s).

BRIEF DESCRIPTION OF THE DRAWINGS

An example of a vented ostomy bag according to the present invention will now be described with reference to the accompanying drawings in which:

FIG. 1 is a cross-section through a bag according to the invention in a vertical orientation;

FIG. 2 is a detail of the upper portion of the bag of FIG. 1, again in vertical cross-section;

DESCRIPTION OF THE PREFERRED EMBODIMENTS

Figure 3:
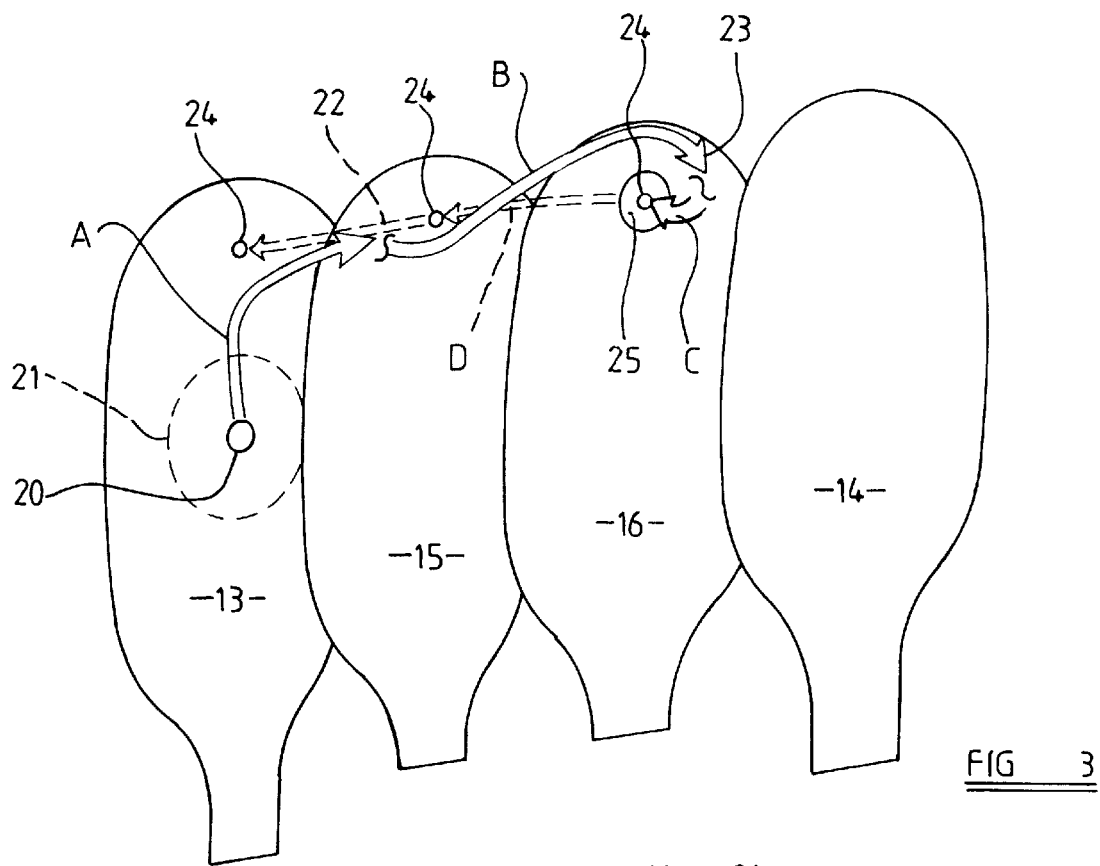
FIG. 3 is an exploded view of the bag of FIG. 1, showing the gas path through the bag.

A vented ostomy bag 10 has a top 11 and a bottom 12. The bag 10 comprises a first outer wall 13, a second outer wall 14, a first intermediate wall 15 and a second intermediate wall 16, the walls are sealed together around their edges to form the bag 10, although a portion is left open at the bottom 12 to enable the bag to be emptied. The first outer wall 13 and first intermediate wall 15 define a first chamber 17, the first intermediate wall 15 and second intermediate wall 16 define a second chamber 18, and the second intermediate wall 16 and second outer wall 14 define a third chamber 19.

Figure 4:
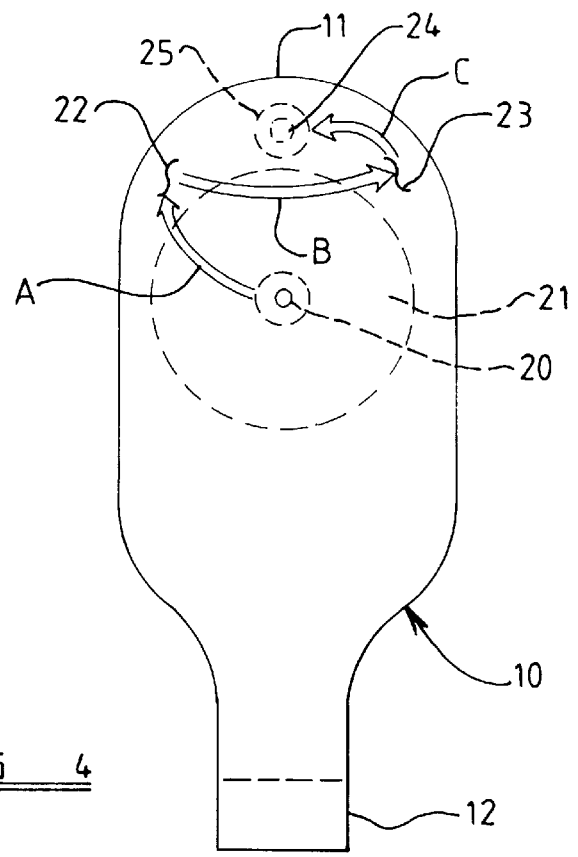
FIG. 4 is a front view of the bag of FIG. 1 again showing the gas path through the bag.

The first and second intermediate walls 15, 16 may be the same dimensions as the first and second outer walls 13, 14, as shown in FIG. 1, or they may be shorter as shown in FIGS. 3 and 4.

The first outer wall is provided with a stoma-receiving opening 20 with around it the means 21 for attachment of the bag 10 to a stoma of a wearer in known fashion, which as it is not part of the present invention will not be described further here. Thus the stoma-receiving opening opens into the first chamber 17 of the bag 10, and the first outer wall is in use the body-side wall.

The first intermediate wall 15 is provided with a first gas vent 22 for the passage of gas through the first intermediate wall 15 from the first chamber 17 to the second chamber 18. The first gas vent 22 comprises an "S" shaped cut in the wall 15, and is located above the stoma-receiving opening 20, and laterally displaced with respect to that opening 20.

The second intermediate wall 16 is provided with a second gas vent 23 for the passage of gas through the second intermediate wall 16 from the second chamber 18 to the third chamber 19. The second gas vent 23 also comprises an "S" shaped cut in the wall 16, and is located above the stomareceiving opening 20, and laterally displaced with respect to both that opening 20 and the first gas vent 22. The first and second gas vents 22, 23 are preferably in line with the filter 25 or located below the gas filter 25.

A gas passage 24 is provided from the third chamber 19 to permit gas to pass out of the bag 10. The gas passage 24 passes through the second intermediate wall 16, the first intermediate wall 15 and the first outer wall 13, these walls all being welded together around the gas passage 24.

The gas passing out of the bag 10 through the gas passage 24 also passes through a gas filter 25 which is designed to remove odour from the gas. The filter 25 is located within the third chamber 19 on the second intermediate wall 16, as illustrated in FIG. 2, such that the gas passes through the filter 25 before passing through the gas passage 24. The exposed face of the filter 25 is covered with an impervious membrane 26, the gas passing into the filter 25 around it's circumferential surface.

A microporous patch 27 may be provided on the exterior of the bag 10 overlaying the gas passage 24. The microporous patch 27 is provided to prevent the filter 25 becoming damp when the exterior of the bag 10 gets wet, for example when the wearer takes a shower.

The walls 13, 14, 15 and 16, may be formed of any appropriate material. Typically they are formed of thermoplastics material which is readily weldable to form the bag 10, to affix the attachment means 21 and to form the gas passage 24 and affix the gas filter 25. The gas filter 25 may also be of any appropriate form and in particular may be of the kind known in the prior art.

The vented ostomy bag 10 according to the invention performs as follows.

When in use the bag 10 is closed at the bottom 12 by means of a clip (not shown) of known kind. The clip may be removed to empty the bag through the open bottom 12, before being replaced for continued use. Generally the bottom 12 will be cleaned with tissues or wipes, inside and outside before the clip is replaced.

When the first and second intermediate walls 15, 16 are shorter (as in FIGS. 3 and 4) they are still retained in the clip when the bag 10 is closed to create the separate chambers. However, the cleaning of the bottom 12 of the bag 10 is a simpler matter for the wearer.

Solids and liquids entering the bag 10 through the stoma-receiving opening 20 tend to fall down the bag 10 within the first chamber 17. Gas also enters the bag 10 through the stoma-receiving opening 20 and tends to rise to the top of the first chamber 17, as illustrated schematically be arrow A in FIGS. 3 and 4. The gas then passes through the first gas vent 22 into the second chamber 18 and across the top of that chamber to the second gas vent 23, as illustrated schematically be arrow B in FIGS. 3 and 4, where it passes through into the third chamber 19. The gas then passes across the top of the third chamber 19 to the gas passage 24, as schematically illustrated by arrow C in FIGS. 3 and 4. The gas then passes through the filter 25 and out of the bag 10 through the gas passage 24, as illustrated schematically by the broken arrow D in FIG. 3.

The provision of the intermediate walls 15 and 16, and the convolution of the path A, B, C from the stoma-receiving opening 20 to the gas passage 24 are designed to minimise the chance of solids or liquids in the bag 10 reaching the filter and reducing it's effectiveness or blocking it entirely.

In addition to the features described above and illustrated in the drawings the portions of the intermediate walls 15, 16 above the stomareceiving opening 20 may be non-smooth to help prevent the walls sticking together if solids or liquids to enter the second and third chambers 18, 19. The non-smooth surface is conveniently formed by embossing of the walls 15, 16 before the bag 10 is constructed.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

What is claimed is:

1. A vented ostomy bag with a gas filter, the bag having a top and a bottom and comprising first and second outer walls sealed around their edges, the first outer wall incorporating a stoma-receiving opening; wherein the bag further comprises first and second intermediate walls also sealed with the first and second outer walls around their edges to provide between the first outer and first intermediate walls a first chamber, between the first and second intermediate walls a second chamber and between the second intermediate and second outer walls a third chamber; a first gas vent being provided in the first intermediate wall between the first and second chambers for the passage of gas there between, a second gas vent being provided in the second intermediate wall between the second and third chambers for the passage of gas there between, and a gas passage being provided from the third chamber out of the bag which passes through the gas filter.

2. An ostomy bag according to claim 1 wherein the walls are formed of thermoplastics material and are sealed at their edges by welding.

3. An ostomy bag according to claim 2 wherein the gas passage is provided trough the second intermediate wall, the first intermediate wall and the first outer wall.

4. An ostomy bag according to claim 3 wherein the gas filter, the second intermediate wall, the first intermediate wall and first outer wall are all welded together to provide the gas passage from the third chamber out of the bag.

5. An ostomy bag according to claim 4 wherein the gas filter is provided within the third chamber on the second intermediate wall.

6. An ostomy bag according to claim 1 wherein the gas filter, first gas vent and second gas vent are all provided between the stoma-receiving opening and the top of the bag.

7. An ostomy bag according to claim 6 wherein the gas filter, first gas vent and second gas vent are laterally disposed with respect to each other.

8. An ostomy bag according to claim 7 wherein the gas filter is located substantially centrally of the width of the bag, the first gas vent is laterally disposed to one side of the gas filter and the second gas vent is laterally disposed to the other side of the gas filter.

9. An ostomy bag according to claim 1 wherein the first and second gas vents comprise "S" shaped cuts in the respective intermediate walls.

10. An ostomy bag according to claim 1 wherein the portions of one or both of the intermediate walls between the ostomy-receiving opening and the top of the bag have surfaces which are non-smooth.

11. An ostomy bag according to claim 10 wherein the non-smooth surface(s) are formed by embossing of the intermediate wall(s).

* * * * *